United States Patent [19]

Evans et al.

[11] Patent Number: 5,203,807
[45] Date of Patent: Apr. 20, 1993

[54] KNEE JOINT PROSTHESIS ARTICULAR SURFACE

[75] Inventors: David L. Evans, Bartlett; Mark S. Gosney, Memphis, both of Tenn.

[73] Assignee: Smith & Nephew Richards Inc., Memphis, Tenn.

[21] Appl. No.: 727,971

[22] Filed: Jul. 10, 1991

[51] Int. Cl.$^5$ .............................................. A61F 2/38
[52] U.S. Cl. ................................................... 623/20
[58] Field of Search .............................. 623/18, 20, 16

[56] References Cited

U.S. PATENT DOCUMENTS 4,911,721  3/1990  Bränemark et al. .................. 623/20
4,959,071  9/1990  Brown et al. .......................... 623/20

FOREIGN PATENT DOCUMENTS 0328463   8/1989  European Pat. Off. .
0346183  12/1989  European Pat. Off. .
2219942  12/1989  United Kingdom .

OTHER PUBLICATIONS

Kärrholm, Johan: "Roentgen Stereophotogrammetry—Review of Orthopedic Applications", *Acta Orthop Scand* 1989, 60(4) pp. 491–503.
"Surgical Technique—Genesis ™ Total Knee System Cruciate-Retaining Primary Technique" (Smith+Nephew Richards brochure).

Primary Examiner—Randall L. Green
Assistant Examiner—D. Willse

[57] ABSTRACT

A knee replacement prosthesis includes a tibial component and a femoral component with improved articular surface geometries. The improved geometries allow substantial internal rotation of the tibial component with respect to the femoral component during at least the first twenty degrees (20°) of flexion. The tibial and femoral components are capable of flexing about an axis that reaches an inclination of from about ten degrees (10°) to about fifty degrees (50°) to the horizontal.

10 Claims, 6 Drawing Sheets

KNEE JOINT PROSTHESIS ARTICULAR SURFACE

BACKGROUND OF THE INVENTION:

1. Field Of The Invention

The present invention relates to knee joint prostheses, and more particularly, to an improved implantable knee joint prosthesis including femoral and tibial components with improved articular surface geometries that allow flexion of the knee about an inclined flexion axis with regard to horizontal, the flexion axis being higher toward the middle of the body and lower toward the outside edge of the body.

2. General Background

In the reconstruction of the anatomical knee joint by total or partial replacement with a prosthetic joint, femoral and tibial prosthetic components provide a knee joint prosthesis in which the articulating or contacting surfaces of the components operate to provide a functioning knee joint.

At the present time, most knee prostheses provide for anteroposterior rotation about a horizontal flexion axis in order to allow movement similar to the anatomical knee joint with the tendons and ligaments of the joint imparting stability and the components affording a certain degree of stability.

Human joints are complex systems which serve a number of functions. Perhaps the most important function is to provide a means of moving body parts for locomotive purposes. The motion provided by most human joints is not simple rotation or translation, but a complex combination of movements.

Perhaps the best known joint with complex motion is the knee. The knee is capable of translation and rotation about three orthogonal axes. Motion is controlled by the collective actions of the articular surface geometries and forces applied to the joint.

Joint replacement devices utilized for pain relief and restoration of function seek to restore normal motion. However, in all cases known to the applicants, the motion allowed by the articular surface geometries (which have been simplified to readily facilitate manufacture and to minimize wear of the articulating components) is abnormally simple. As a result, a "kinematic conflict" may develop at the articular surfaces because the motion allowed by the implants may not be compatible with their relative positions as dictated by external forces.

A kinematic conflict may lead to excessive stresses between the articulating components, leading to destruction of one or both surfaces. Destruction of the surfaces will result in high wear rates, the release of wear debris into the joint, and undesirable tissue reactions. The symptoms are likely to be sufficiently severe to require surgical removal and replacement of the implants, with all of the inherent risks and injuries to the patient.

The above-described problem is particularly true of the reconstructed knee joint in movements from full extension to about twenty degrees of flexion during load bearing activities such as walking. During these activities the normal femur externally rotates about five to fifteen degrees (5°-15°) on the surface of the tibia as the knee flexes twenty degrees (20°). All total knee replacements known to the applicants will not allow this motion to occur without the aforementioned kinematic conflict and negative consequences.

Prior art approaches to this problem include utilizing incongruent articular surface geometries (except for line contact). In these designs, congruence of the articular surfaces is limited to one plane (usually the frontal plane) and results in a line contact between the components. The elasticity of one of the articulating members (usually a polymer tibial component) allows the line contact to expand to an area contact if contact forces are sufficiently large. However, the area contact due to elastic deformation is not sufficient to protect the polymer from excessive stresses and the resulting creep and wear phenomena reported in the literature.

Geometries of this type are advantageous in that they allow relative internal/external rotations of the components without large external forces being applied. However, the contact area between the components diminishes further under these circumstances because the congruent profiles are no longer aligned.

Another approach to this problem has been to simply ignore it, by configuring the articular surface geometries for an area contact and restricting congruent motion to one plane (i.e. flexion and extension only). This approach is advantageous in the sense that it maximizes contact area in pure flexion/extension movements, thus should minimize creep and wear of the polymer.

Designs of this type will not allow internal/external rotation during flexion and extension without substantial effort and stresses between the articulating components. As in the former case, excessive stresses lead to wear and creep of the polymer component and early failure of the joint replacement.

There is yet another approach to this problem known as the meniscal bearing prosthesis. Meniscal bearing prostheses feature an area contact at the articular interface because of congruent surfaces (similar to the Tricon knee). To obviate the problem of excessive constraint inherent in these designs, the polymer insert(s) is designed to be mobile on the surface of a metal plate which is attached to bone. The mobility of the insert(s) helps to avoid a kinematic conflict at the articular interface by allowing the bones to adjust their relative positions according to external forces while maintaining an area contact at the articular interface.

Examples of meniscal bearing designs can be found for example in the Oxford knee (European patent No. 327387-A) and New Jersey Knee (U.S. Pat. Nos. 4,309,778, 4,340,978, and 4,470,158). These designs have several disadvantages. First, the polymer inserts have a tendency to dislocate, requiring surgical intervention for replacement. Second, if all ligamentous structures are not preserved and functional, these designs will not provide the stability required for good function and patient confidence. Additionally, the New Jersey design, while featuring mobile inserts, does not allow the desired motion, because internal/external rotations of the inserts are centered on the metal tibial tray, and not lateral to the center. This inconsistency may lead to a kinematic conflict (especially if all ligamentous structures are preserved and functional).

An example of another prior art type of knee joint presently utilized is disclosed e.g. in U.S. Pat. No. 4,298,992, issued on Nov. 10, 1981 for a "Posteriorly Stabilized Total Knee Joint Prosthesis" wherein there is included a femoral component utilizing a pair of laterally spaced apart condylar portions each of which having an external surface convexly curved to match generally the lateral profile of the anatomical femoral condyle.

U.S. Pat. No. 4,298,992 further discloses a tibial component and a platform portion including spaced apart concavities for receiving each of the condylar portions of the femoral component. The post extends from the tibial plateau into the intracondylar recess of the femoral component so that upon full flexion of the joint, the knee joint is stabilized between the tibial post and femoral recess. The U.S. Pat. No. 4,298,992 addresses the prevention of translocation of the knee during flexion.

SUMMARY OF THE PRESENT INVENTION

The present invention seeks to provide tibial and femoral components with improved articular surface geometries which would enable the tibia to rotate with respect to the femur.

An object of the invention is to create an artificial joint articular surface geometry which will allow internal/external rotations of the joint during flexion/extension movements, while preserving a higher degree of congruence between the articulating surfaces than that allowed by conventional joint replacements.

By allowing combinations of movements with a high degree of congruence between articulating components, contact stresses between components will be reduced, resulting in less creep and wear (ceterus paribus).

The femoral component and tibial components are designed to articulate with one another during normal movements of the knee. The motion which typically occurs during the first twenty degrees of flexion includes up to fifteen degrees (15°) of internal rotation of the tibial component. This combination of flexion and internal rotation with substantially congruent surface area contact between components is facilitated by the special articular surface geometries.

The tibial surface is created by swinging a profile about an axis inclined at an angle between ten and fifty degrees (preferably about thirty-six degrees) with respect to the horizontal reference plane. The inclined axis passes through the horizontal reference plane at a position lateral to the center of the knee. The profile is swept in anterior and posterior directions from the starting position through a sufficiently large arc to completely cover the surface of the largest tibial component required. In the lateral compartment, the profile may not be swept anteriorly about the inclined axis, depending upon the need to match the shape with the femoral component. This change will not affect the kinematics of the tibiofemoral articulation.

The femoral articulating surface is created in a similar manner. A profile is swept about the same inclined axis as with the tibial surface. The profile is swept in anterior and posterior directions through a sufficiently large arc to provide for substantially congruent contact between the femoral and tibial surfaces through the first twenty to thirty degrees of flexion of the femoral component. In the lateral compartment, the profile may not be swept anteriorly about the inclined axis, depending upon the need to match the shape with the tibial component. This change will not affect the kinematics of the tibiofemoral articulation.

For flexion greater than twenty degrees, the posterior condyles of the femoral component begin to articulate with the tibial surface. During this motion, the contact is a small surface area contact, due to the geometries and elasticities of the contacting surfaces. Flexion of the femoral component beyond twenty degrees occurs about an axis which is more or less parallel to the posterior condylar axis.

Because of the inclined axis for the first twenty degrees of flexion, the surfaces of the tibial and femoral components can maintain a large surface area of contact, without a kinematic conflict. The large area of contact will result in lower contact stresses and, therefore reduce creep and wear of the articular surfaces. Reducing damage will extend the life of the joint replacement and reduce the likelihood that revision surgery will be necessary. This benefit is realized without a compromise in stability (as in meniscal bearing designs), allowing the articular geometry to be used in knees where one or both cruciate ligaments are absent or non-functional.

Therefore, it is an object of the present invention to provide an improved knee prosthesis including tibial and femoral components with improved articulating surface geometries.

It is still another object of the present invention to provide a knee joint prosthesis wherein the femoral and tibial components provide improved articular surface geometries that allows rotation (as much as fifteen degrees) of one component with respect to the other about an inclined flexion axis. It is still a further object of the present invention to provide a total knee joint prosthesis which includes improved articular surface geometries wherein articular surfaces are formed by rotating a knee prosthesis profile about an inclined axis through a preferred angle of between twenty and forty degrees (20°-40°) of rotation to create an articular surface which allows the tibial and femoral components to rotate about an inclined flexion axis while maximizing contact area therebetween to lower stresses and prolong prostheses life. The profile, however, could be rotated through an angle of between one and one hundred twenty degrees (1°-120°), though twenty to forty degrees (20°-40°) is preferred.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein.

DETAILED DESCRIPTION OF THE PREFERRED EMBODIMENT

The preferred embodiment of the knee joint prosthesis of the present invention is illustrated in the figures by the numeral 10. Knee prosthesis 10 includes a tibial component 10-A and a femoral component 10-B. The tibial component 10-A has an upper most tibial articular surface 11 which bears against a femoral articular surface 21 of the femoral component 10-B.

Figure 7:
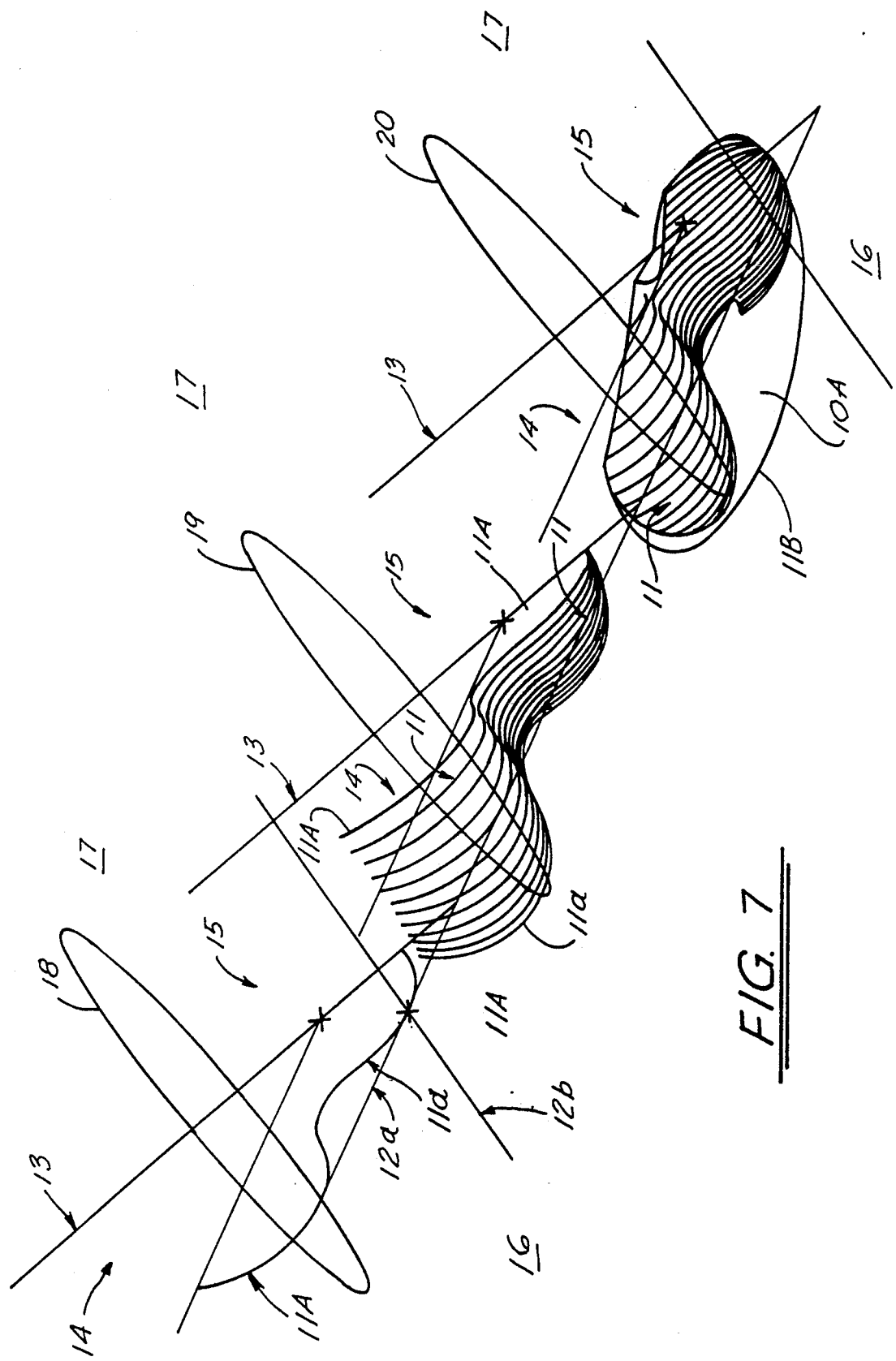
FIG. 7 is a perspective schematic view of the preferred embodiment of the apparatus of the present invention illustrating generation of the tibial articular surface for a bicompartmental knee prosthesis.

In FIG. 7, the tibial articular surface 11 is illustrated for a tibial component 10-A having a bicompartmental or two condylar surface construction. FIG. 7 illustrates a generation of the tibial articular surface 11 using a horizontal reference plane 12 defined by the lines 12-A, 12-B. The line 13 represents an inclined axis, inclined with respect to the horizontal plane 12 by a measure of for example thirty degrees (30°). In the preferred embodiment, the inclined axis is inclined at an angle of between ten and fifty degrees (10°-50°).

In FIG. 7, the medial 14 and lateral 15 side of the patient's knee is shown for each generation of the tibial articular surface which is illustrated by the three rotational paths 18, 19 and 20. In the left hand side of FIG. 7, an initial rotational path 18 is shown with a single curved line 11-A representing the tibial articular surface profile. While the profile 11-A consists of three tangent curves, the profile may take other forms, such as two straight lines connected by one or more curves or straight lines (i.e. the form of the profile itself is not critical, as long as it meets other general requirements for a knee prosthesis). In the middle of FIG. 7, the profile 11-A has been rotated through a measure of approximately forty degrees (40°) so that a plurality of lines 11-A represent a generation of the surface 11 about the axis 13. In the right hand side of FIG. 7, the completed articular surface 11 is shown surrounded by the peripheral edge 11-B of the tibial component 10-A. It should be understood that the tibial component 10-A could for example be of a polymer material and of a desired outer peripheral shape 11B and of a desired thickness.

Figure 8:
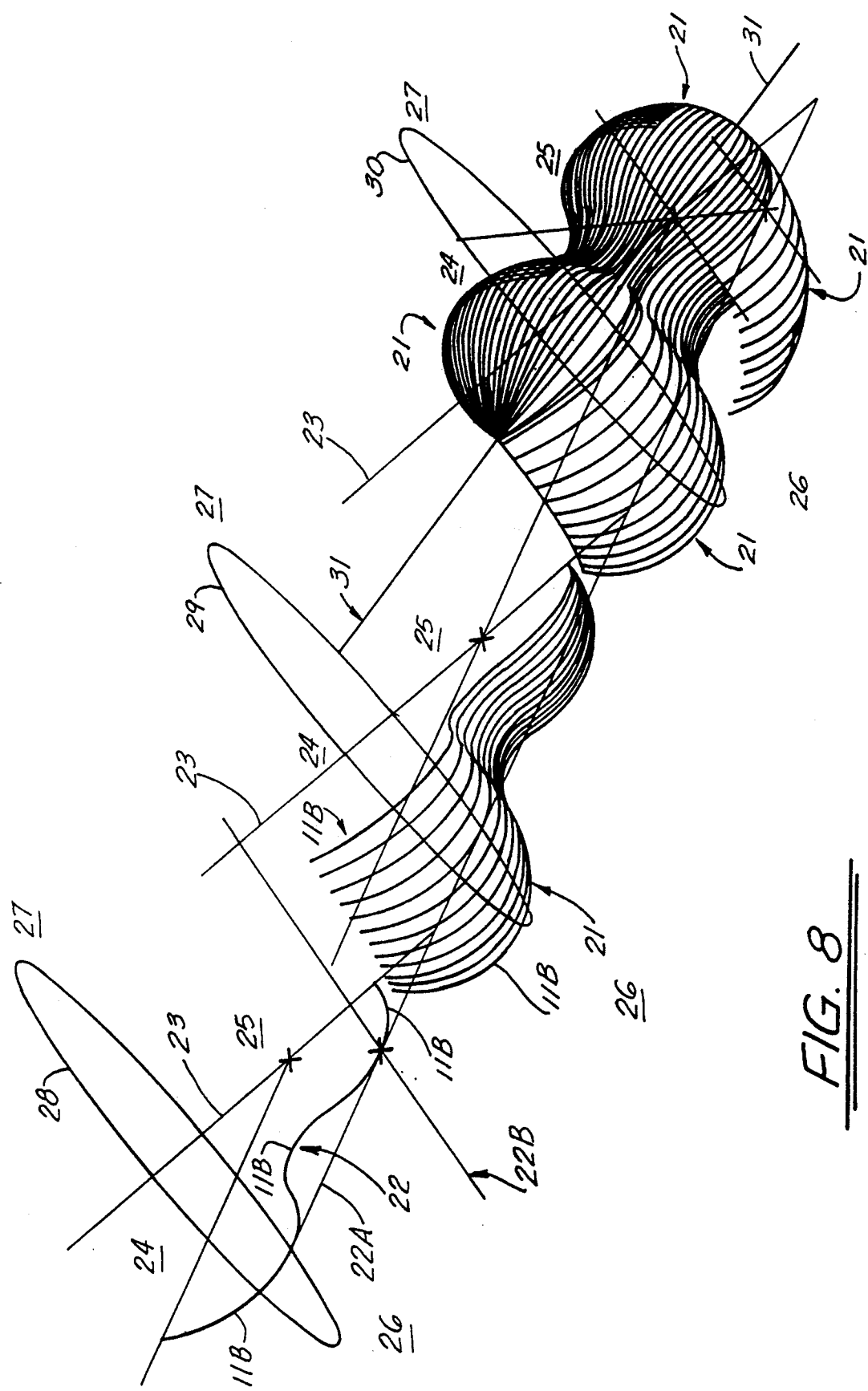
FIG. 8 is a perspective schematic view of the preferred embodiment of the apparatus of the present invention illustrating the femoral articular surface for a bicompartmental knee prosthesis.

In FIG. 8, the femoral articular surface 21 is illustrated as is the method of generating the femoral articular surface 21. In FIG. 8, the horizontal plane 22 is defined by the perpendicular lines 22A, 22B. Inclined axis 23 defines an angle of between 10 and fifty degrees with respect to horizontal plane 22 and represents the axis about which the profile line 11B is rotated as represented by the rotational paths 28, 29, and 30.

Figure 1:
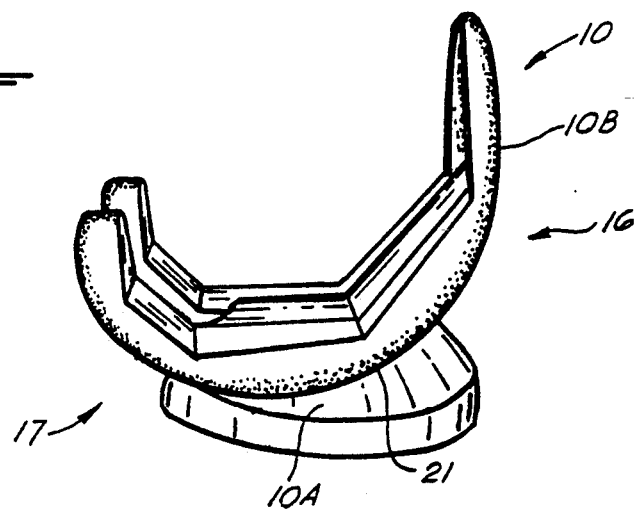
FIG. 1 is a side view of the preferred embodiment of the apparatus of the present invention in full extension position.
Figure 2:
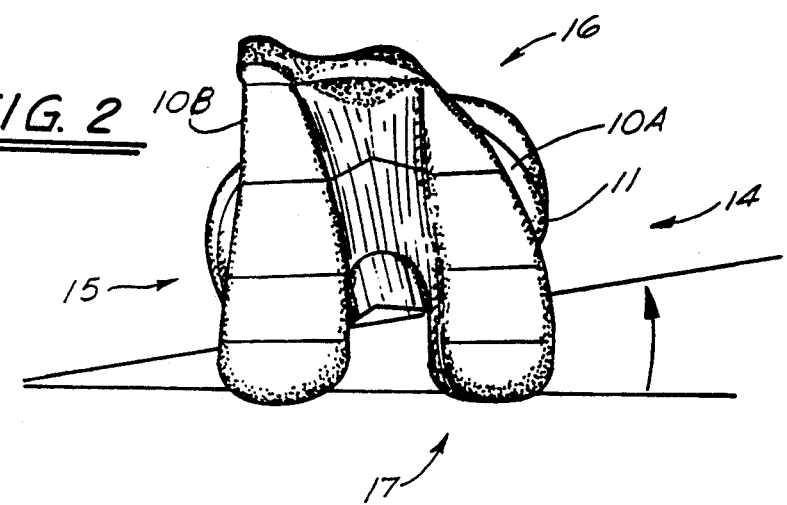
FIG. 2 is a top view of the preferred embodiment of the apparatus of the present invention in full extension position.
Figure 3:
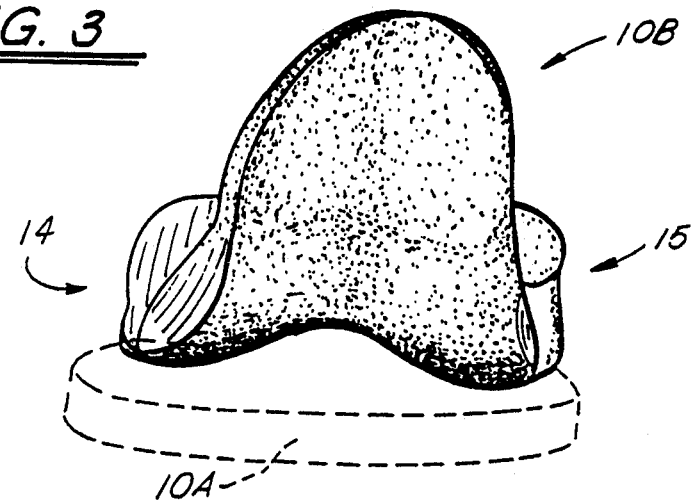
FIG. 3 is a front view of the preferred embodiment of the apparatus of the present invention in full extension position.
Figure 4:
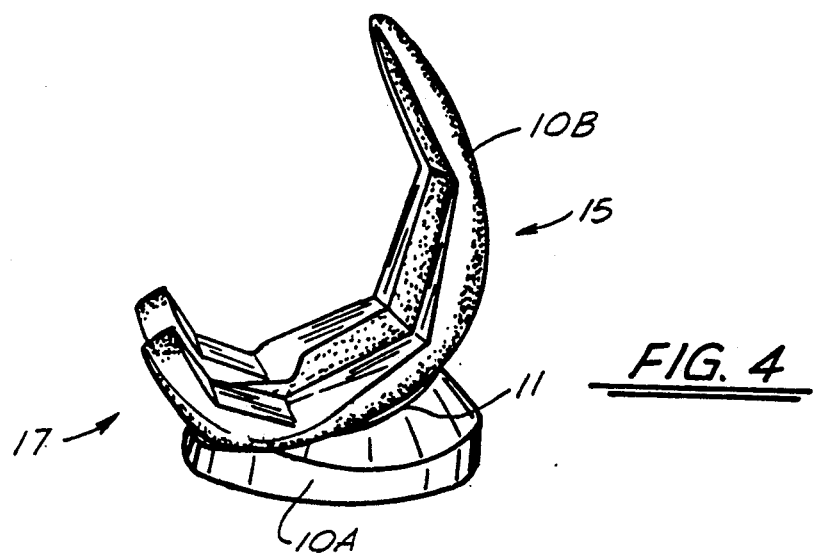
FIG. 4 is a side view of the preferred embodiment of the apparatus of the present invention on a twenty degree (20°) flexion position.
Figure 5:
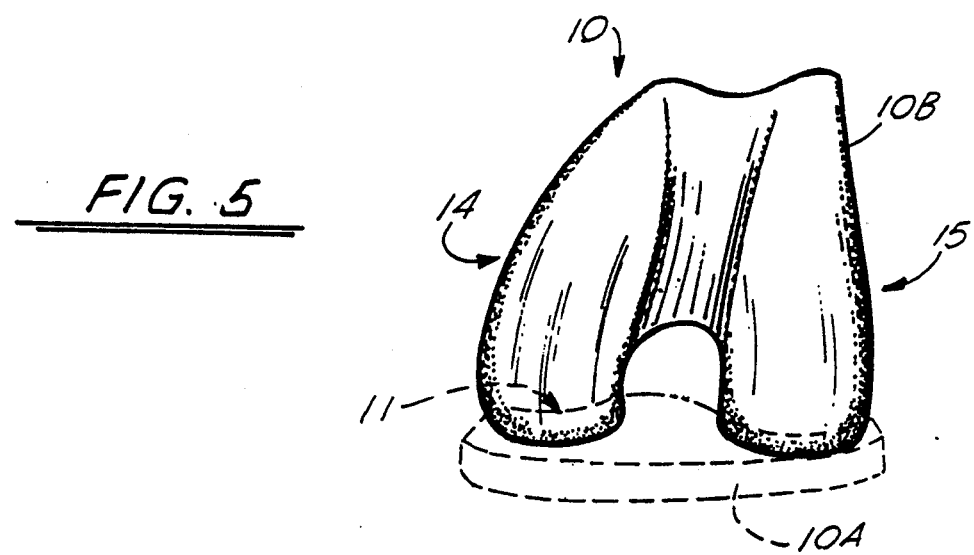
FIG. 5 is a front view of the preferred embodiment of the apparatus of the present invention in ninety degree flexion position.
Figure 6:
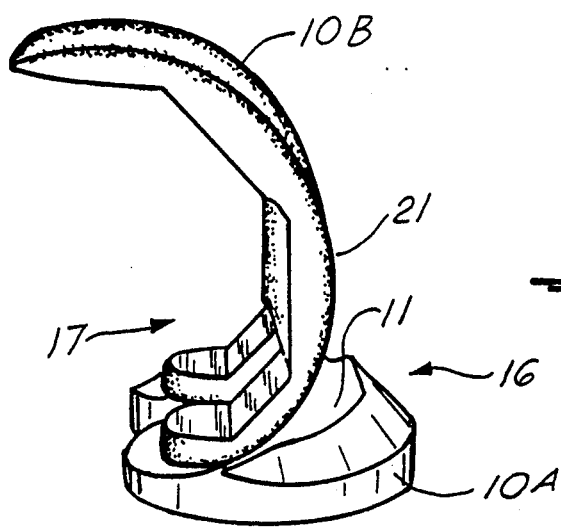
FIG. 6 is a side view of the preferred embodiment of the apparatus of the present invention in a ninety degree (90°) flexion position.
Figure 9:
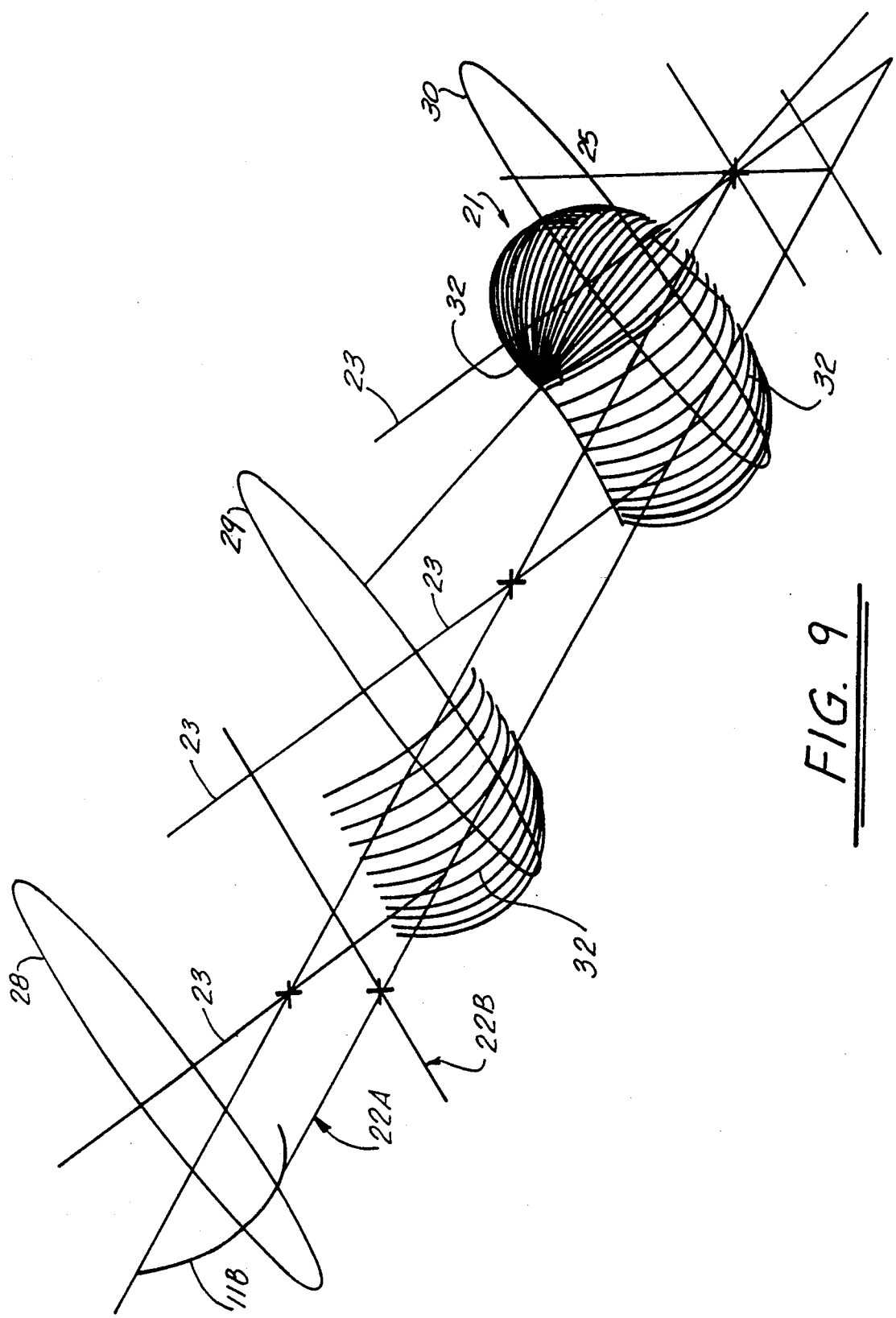
FIG. 9 is a perspective schematic view of the preferred embodiment of the apparatus of the present invention illustrating generation of the femoral articular surface for a unicompartmental knee prosthesis.
Figure 10:
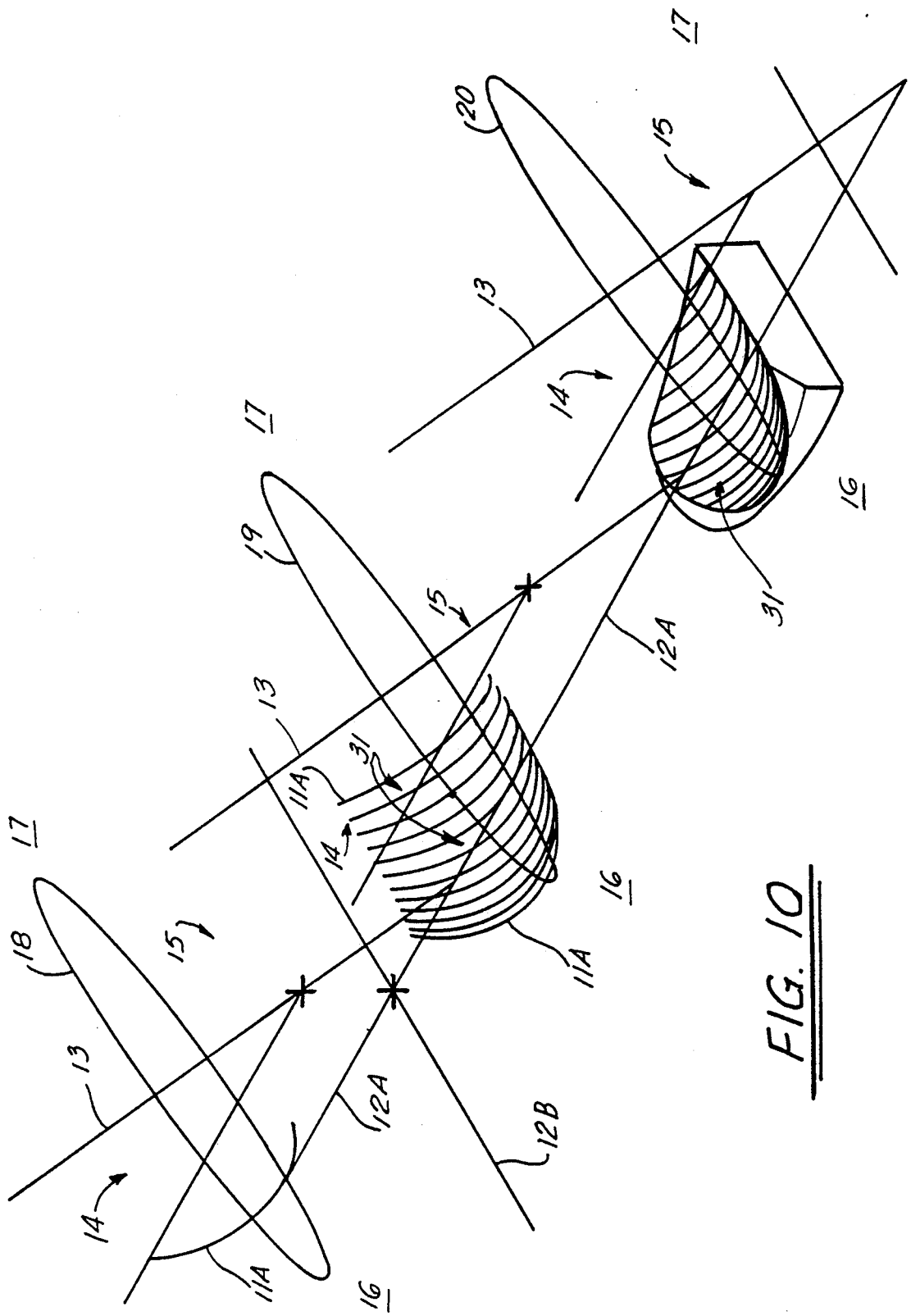
FIG. 10 is a perspective schematic view of the preferred embodiment of the apparatus of the present invention illustrating generation of the tibial articular surface for a unicompartmental knee prosthesis.

The profile 11B represents a profile for forming a bicompartmental knee or two condylar knee prosthesis. In the left hand side of FIG. 8, the path of rotation 28 is firstly illustrated with regard to the single line profile 11B. In figure 8, the profile 11B has been rotated through a measure of approximately forty degrees (40°) forming the articular surface 21. In the right hand side of FIG. 2, the tibiofemoral articular surface 21 has been completed, by the addition of a portion 32 posteriorly of the line 31—31, and not a portion of the surface 21 generated by rotating the profile 11B about the axis 23. In FIGS. 9 and 10, tibial and femoral articular surfaces respectively are shown, to illustrate the present invention in a single compartmental knee prosthesis. In FIG. 9, the tibial articular surface 33 is illustrated while in FIG. 10, the single condylar femoral surface 35 is illustrated.

| PARTS LIST | |
|---|---|
| PART NUMBER | DESCRIPTION |
| 10 | knee prosthesis |
| 11 | tibial articular surface |
| 12 | horizontal line |
| 13 | inclined axis |
| 14 | medial side of knee |
| 15 | lateral side of knee |
| 16 | anterior side of knee |
| 17 | posterior side of knee |
| 18 | rotational path, initial |
| 19 | rotational path, middle |
| 20 | rotational path, complete |
| 21 | femoral articular surface |
| 22 | horizontal line |
| 23 | inclined axis |
| 24 | medial side |
| 25 | lateral side |
| 26 | anterior side |
| 27 | posterior side |
| 28 | rotational path |
| 29 | rotational path |
| 30 | rotational path |
| 31 | single condylar tibial surface |
| 32 | single condylar femoral surface |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A prosthesis for surgical implantation for replacement of a patient's knee having two spaced apart condylar portions, or for replacement of a portion thereof comprising:
    a) a tibial component that includes one or more concave tibial condylar articulating surfaces;
    b) a femoral component that includes one or more distal femoral condyles, each with a convex femoral condylar articulating surface that articulates against one of said tibial condylar articulating surfaces of the tibial component;
    c) the concave tibial and convex femoral condylar articulating surfaces being correspondingly shaped to define during at least the first few degrees of flexion from a beginning position a flexion axis with an inclination of from about ten degrees (10°) to about fifty degrees (50°) with respect to a transverse plane tangent to distal femoral condyles; and
    d) the concave tibial and convex femoral condylar articulating surfaces being correspondingly shaped and conforming articular surfaces through the first few degrees of flexion from a beginning fully extending position, with substantial congruent surface area contact between said components.

2. The apparatus of claim 1 wherein the femoral component is capable of external rotation with respect to the tibial component, at least during the first few degrees of flexion from a beginning fully extending position.

3. The apparatus of claim 1 wherein a medial side of the prosthesis and lower toward a lateral side of the prosthesis.

4. The apparatus of claim 1 wherein the tibial component includes a single condylar articulating surface.

5. The apparatus of claim 1 wherein the femoral component includes a single condylar articulating surface.

6. The apparatus of claim 1 wherein the tibial component has a pair of spaced apart condylar articulating surfaces.

7. The apparatus of claim 1 wherein the femoral component has a pair of spaced apart condylar articulating surfaces.

8. The apparatus of claim 1 wherein the condylar articulating surfaces are generated by rotating a curved line profile about an inclined axis that is inclined between ten (10) and fifty (50) degrees with respect to the distal femoral condyles in the frontal plane.

9. The apparatus of claim 8 wherein the curved profile is rotated about the inclined axis by a measure between one and one hundred twenty degrees (1°–120°).

10. A knee joint prosthesis comprising:

a) a tibial component with a concave tibial articulating condylar surface;

b) a femoral component with a convex femoral articulating condylar surface that includes one or more distal femoral condyles;

c) means for attaching the tibial component to a patient's tibia;

d) means for attaching the convex femoral component to the patient's femur;

e) the concave tibial and convex femoral components being correspondingly shaped to define an inclined flexion axis with an inclination of from about ten degrees (10°) to about fifty degrees (50°) with respect to a transverse plane tangent to the distal femoral condyles during at least the first few degrees of flexion from a beginning fully extending position, with substantial congruent surface area contact between said components; and f) the concave tibial and convex femoral articulating condylar surfaces being correspondingly shaped conforming articular surfaces to define said flexion axis; and g) wherein substantial internal rotation of the tibial component is enabled with respect to the femoral component during flexion, with substantial congruent area contact maintained between the conforming concave tibial and convex femoral condylar articulating surfaces.

* * * * *

UNITED STATES PATENT AND TRADEMARK OFFICE
CERTIFICATE OF CORRECTION

PATENT NO.  : 5,203,807
DATED       : April 20, 1993
INVENTOR(S) : David L. Evans and Mark S. Gosney It is certified that error appears in the above-identified patent and that said Letters Patent is hereby corrected as shown below:

IN THE CLAIMS: COLUMN 7, LINES 5-7, SHOULD READ:

3. The apparatus of claim 1 wherein <u>the flexion axis is higher toward</u> a medial side of the prosthesis and lower toward a lateral side of the prosthesis.

Signed and Sealed this

Fourteenth Day of June, 1994

Attest:

BRUCE LEHMAN

*Attesting Officer*     *Commissioner of Patents and Trademarks*